| United States Patent [19] | [11] | 4,331,820 |
|---|---|---|
| Taguchi et al. | [45] | May 25, 1982 |

[54] CIS-6-UNDECENE-1-CHLORIDE AND A METHOD FOR THE PREPARATION THEREOF

[75] Inventors: Kenichi Taguchi; Akira Yamamoto; Toshinobu Ishihara; Nobuo Takasaka; Hisashi Shimizu, all of Joetsu, Japan

[73] Assignee: Shin-Etsu Chemical Co., Ltd., Tokyo, Japan

[21] Appl. No.: 222,982

[22] Filed: Jan. 7, 1981

[30] Foreign Application Priority Data

Jan. 14, 1980 [JP] Japan .................................. 55-2986

[51] Int. Cl.$^3$ ...................... C07C 17/26; C07C 21/04
[52] U.S. Cl. .................................. 570/189; 570/217; 570/219
[58] Field of Search ........................ 570/189, 217, 219

[56] References Cited

U.S. PATENT DOCUMENTS 3,459,819  8/1969  Suzuki ................................ 570/189
4,292,454  9/1981  Cardenas et al. ................... 570/189

OTHER PUBLICATIONS

Jacobson, Insect Sex Pheromones, 1972, p. 229.

Primary Examiner—Delbert E. Gantz
Assistant Examiner—Joseph A. Boska
Attorney, Agent, or Firm—Toren, McGeady and Stanger

[57] ABSTRACT

A novel compound cis-6-undecene-1-chloride is prepared by reacting cis-3-octene-1-chloride with metallic magnesium to give a Grignard reagent of the chloride and then reacting the Grignard reagent with 1-bromo-3-chloropropane in the presence of a lithium copper chloride as a catalyst. The inventive compound is a useful intermediate compound for the synthetic preparation of several kinds of so-called sexual pheromone compounds of noxious insects. As an example of such sexual pheromone compounds, the synthetic preparation of cis-9-tetradecenyl acetate is described.

4 Claims, No Drawings

CIS-6-UNDECENE-1-CHLORIDE AND A METHOD FOR THE PREPARATION THEREOF

BACKGROUND OF THE INVENTION

The present invention relates to cis-6-undecene-1-chloride, which is a novel compound hitherto not known or not described in any prior art literatures, and also to a method for the synthetic preparation of the same compound.

As is well known, extermination of various kinds of noxious insects not only in household but also agriculture and forestry is carried out less and less by use of chlorine-containing or phosphorus-containing organic chemicals which may cause serious environmental pollution or a health problem in human body. Instead, one of the promising chemical means for the extermination of noxious insects is the use of the so-called sexual pheromones. A sexual pheromone is a secretion of the insect of a sex and attracts the insects of the other sex of the same species even in an extremely small amount.

Several of the sexual pheromones have already been investigated chemically in detail and their chemical structures have been established. Examples of them are: cis-7-dodecenyl acetate; cis-9-tetradecenyl acetate; cis-11-hexadecenyl acetate; cis-11 hexadecenol; cis-11-hexadecenal; and cis-3-cis-13-octadecadienyl acetate and their use for the extermination of the respective noxious insects is now on the way of development.

These compounds of definite chemical structures can of course be prepared by a chemical method of synthesis but economically advantageous methods for the synthetic preparation of them have not yet been proposed.

SUMMARY OF THE INVENTION

Thus, the inventors have conducted investigations with an object to develop an economically feasible way for the synthetic preparation of the above named sexual pheromone compounds and, in the course of their invesigations, arrived at a discovery of a novel compound which is useful as an intermediate for the synthesis of the sexual pheromone compounds.

The inventive novel compound discovered by the inventors, with which the above named sexual pheromone compounds can be synthesized ecomonically in high yields, is cis-6-undecene-1-chloride expressed by the structural formula

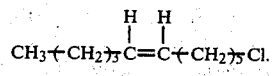

This compound can be prepared by the synthetic route comprising the steps of (1) the formation of cis-3-octenyl magnesium chloride by the reaction of cis-3-octene-1-chloride and metallic magnesium in tetrahydrofuran and (2) reacting the above prepared Grignard reagent with 1-bromo-3-chloropropane in the presence of a lithium copper chloride LiCuCl$_2$ or Li$_2$CuCl$_4$.

DETAILED DESCRIPTION OF THE PREFERRED EMBODIMENTS

As is mentioned above, the starting material of the synthetic preparation of the inventive cis-6-undecene-1-chloride is cis-3-octene-1-chloride, which in turn is prepared starting with butylacetylene via the synthetic route given below. In the following reaction equations, Me denotes a methyl group.

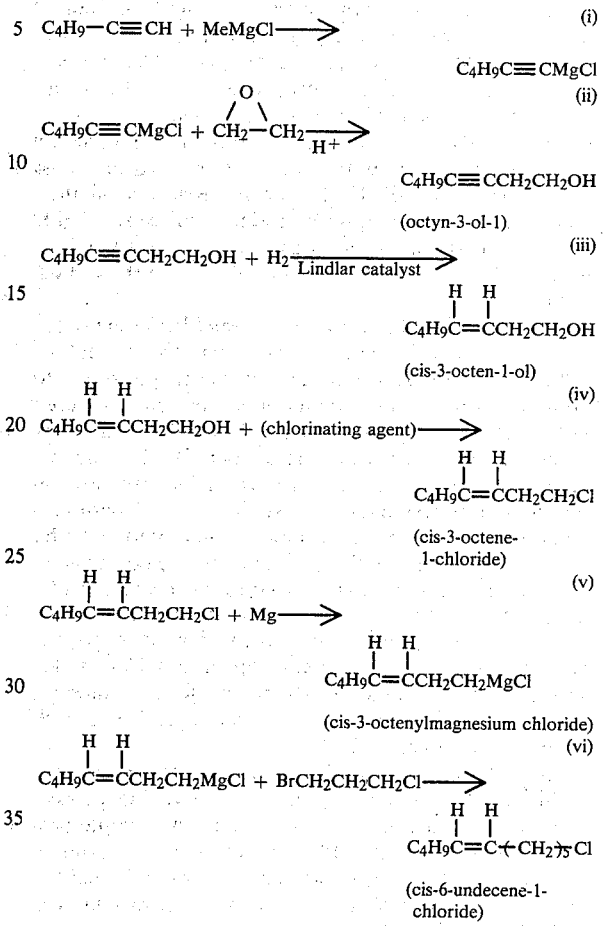

The reactions expressed by the above given equations are now described in detail.

In the first place, butylacetylene is added dropwise into methylmagnesium chloride in tetrahydrofuran prepared in a conventional manner and kept at a temperature in the range from 30° to 60° C. to be reacted into butylacetylene magnesium chloride (reaction (i)).

Into the solution of the Grignard reagent obtained above and kept at 0° to 60° C., ethylene oxide is added dropwise preferably in an amount of 1.6 to 3 times by moles based on the starting butylacetylene and the reaction mixture is hydrolyzed by contacting with an aqueous acidic solution followed by distillation to give 3-octyn-1-ol (reaction (ii)). The yield is usually 80 to 85% of the theoretical value.

The hydrogen reduction of this 3-octyn-1-ol is carried out by dissolving the compound in n-hexane with addition of 3 to 20% by weight of a Lindlar catalyst and introducing hydrogen at room temperature with agitation (reaction (iii)). Removal of the catalyst by filtration and n-hexane by distillation from the reaction mixture gives cis-3-octen-1-ol in an almost quantitative yield.

Chlorination of this cis-3-octen-1-ol is carried out with a chlorinating agent such as thionyl chloride to give cis-3-octene-a-chloride in a yield of 85 to 90% of the theoretical value. (reaction (iv)).

The above obtained cis-3-octene-1-chloride is reacted with metallic magnesium in anhydrous tetrahydrofuran at 40° to 60° C. to give cis-3-octenylmagnesium chloride (reaction (v)).

The Grignard reagent thus obtained in tetrahydrofuran is then cooled to room temperature with addition of a lithium copper chloride, i.e. dilithium copper tetrachloride $Li_2CuCl_4$ or lithium copper dichloride $LiCuCl_2$, and 1-bromo-3-chloropropane is added dropwise into the mixture at 0° to 40° C. under agitation (reaction (vi)). The salt as the by product is removed by filtration or washing with water and tetrahydrofuran as the solvent is distilled off from the reaction mixture. The residue is distilled under reduced pressure to give the desired cis-6-undecene-1-chloride having a purity of at least 98% in a yield of 85 to 90% of the theoretical value.

The amount of the anhydrous tetrahydrofuran used in the reaction (v) should be at least equimolar to the metallic magnesium and preferably in the range from 3 to 20 times by moles. Dilithium copper tetrachloride used as the catalyst in the reaction (vi) is readily obtained by admixing lithium chloride and copper (II) chloride in a molar ratio of 2:1 in tetrahydrofuran while lithium copper dichloride is obtained in a similar manner with lithium chloride and copper (I) chloride in a ratio of 1:1 by moles. The amount of the lithium copper chloride catalyst is in the range from 0.001 to 0.1 mole or, preferably, from 0.003 to 0.02 mole per mole of the metallic magnesium used in the preparation of the Grignard reagent. It is preferable that the lithium copper chloride is dissolved in advance in tetrahydrofuran and the solution is added to the reaction mixture containing cis-3-octenylmagnesium chloride.

As is described above, the inventive cis-6-undecene-1-chloride is synthetically prepared with inexpensive and readily available starting materials in a simple procedure, of which the yield of the respective intermediate compound in each of the steps is very high, and the purity of the objective compound is sufficiently high to be 98% or higher.

Following are the examples to illustrate the method for the preparation of the inventive compound as well as characterization thereof.

EXAMPLE 1

Into a reaction vessel of 2 liter capacity were taken 24.3 g of metallic magnesium, 360 g of anhydrous tetrahydrofuran and a bit of iodine and the reaction mixture was further admixed with 2 g of ethyl bromide and heated to 50° C. with agitation. Then 146.5 g of cis-3-octene-1-chloride were added dropwise into the reaction mixture kept at the same temperature over a period of 2 hours and agitation of the reaction mixture was further continued for 1 hour followed by cooling to 20° C.

Into the thus obtained reaction mixture containing the Grignard reagent was added a solution of dilithium copper tetrachloride in tetrahydrofuran, which had been prepared in advance by dissolving 430 mg of lithium chloride and 676 mg of copper (II) chloride in 100 g of tetrahydrofuran, and further 158 g of 1-bromo-3-chloro-propane were added dropwise over a period of about 2 hours into the reaction mixture kept at a temperature of 15° to 20° C. by cooling with ice under agitation. After completion of the addition of 1-bromo-3-chloropropane, the mixture was heated to 40° C. and kept for 1 hour at the same temperature to complete the reaction followed by cooling to room temperature and removal of the precipitated salt and the catalyst by filtration. The filtrate solution was stripped of tetrahydrofuran and subjected to distillation under reduced pressure to give a fraction boiling at 84° C. under a pressure of 2 mmHg.

The above obtained product was analyzed by the mass spectroscopy, NMR spectroscopy and infrared absorption spectroscopy and identified to be the desired cis-6-undecene-1-chloride from the analytical results given below and the purity of the fraction was 98% as determined by gas chromatography. The above yield of the objective compound was about 90% based on the amount of cis-3-octene-1-chloride.

(Results of the analyses)

(a) Mass spectrum: m/e (relative intensity of the peaks)

The peaks marked with (*) are accompanied by the respective isotopic peaks for the $^{37}Cl$ isotope.

188* (14); 160* (1); 152 (1); 146* (1); 132* (3); 123 (5); 118* (6); 104* (17); 97 (14); 95 (12); 83 (18); 81 (20); 70 (26); 69 (38); 67 (30); 56 (35); 55 (100); 41 (63).

(b) Proton NMR spectrum: δ p.p.m.

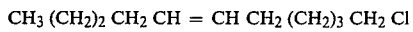

(a)   (b)   (c)   (d)   (e)   (f)   (g)   (h)

(a) 0.92; (b) 1.3 to 1.6; (c) 2.01; (d) 5.35; (e) 5.35; (f) 2.01; (g) 1.3 to 1.6; (h) 3.49

(c) Infrared absorption spectrum: $cm^{-1}$

3003; 2960; 2930; 2857; 1660; 1470; 1413; 1387; 1350; 1320; 1998; 1110; 1065; 1038; 972; 925

EXAMPLE 2

Into a reaction vessel of 1 liter capacity were taken 24.3 g of metallic magnesium, 340 ml of tetrahydrofuran and a bit of iodine and methyl chloride was blown into the reaction mixture under agitation while the temperature of the mixture was kept at 40° to 50° C. by cooling with ice. Then the reaction mixture was heated to about 50° C. and 65 g of butylacetylene were added dropwise into the reaction mixture kept at the same temperature. As the butylacetylene was dropped, gaseous methane was produced. After the end of the addition of butylacetylene, the reaction mixture was further agitated for additional 2 hours with the temperature kept at 50° C.

Thereafter, the reaction mixture was cooled down to a temperature of 10° C. or below and 100 g of ethyleneoxide were gradually added dropwise to the mixture at a rate that the temperature of the mixture did not exceed 40° C. followed by further agitation for 1 hour at about 30° C. The thus obtained reaction mixture was poured into 1 liter of an aqueous solution containing 300 g of ammonium chloride and 200 ml of concentrated hydrochloric acid to effect hydrolysis followed by separation into aqueous and organic phases. Distillation of the organic solution under reduced pressure gave 86 g of 3-octyn-1-ol boiling at 75° C. under a pressure of 5 mmHg. The yield was about 85% of the theoretical value.

Hydrogen gas was blown into a solution prepared by dissolving 126 g of 3-octyn-1-ol in 100 ml of n-hexane with admixture of 10 g of a Lindlar catalyst and 10 g of pyridine and the introduction of hydrogen was continued for about 4 hours when absorption of hydrogen had ceased. Removal of solid matter from the reaction mixture by filtration and stripping of n-hexane gave cis-3-octen-1-ol, which was dissolved in a mixture of 250 g of methylene chloride and 111 g of triethylamine.

Then 131 g of thionyl chloride were added to the solution kept at 10° C. or below dropwise under agitation and, after the end of the addition of thionyl chloride, the reaction mixture was further agitated for 1 hour with the temperature raised to 40° C.

The thus obtained reaction mixture was poured into 500 ml of water with agitation and the organic solution taken by phase separation was washed with 5% aqueous solution of sodium hydroxide and subjected to distillation under reduced pressure to give 127 g of a fraction boiling at 70° C. under a pressure of 30 mmHg which was identified to be cis-3-octene-1-chloride. The above given yield was about 87% of the theoretical value based on the amount of 3-octyn-1-ol.

Following example is to illustrate derivation of a sexual pheromone compound from the inventive cis-6-undecene-1-chloride.

EXAMPLE 3

A Grignard reagent was prepared with 188.5 g of cis-6-undecene-1-chloride obtained in Example 1. The procedure for the preparation of this Grignard reagent was similar to the process for the preparation with cis-octene-1-chloride. After the reaction of this Grignard reagent with 1-bromo-3-chloropropane, the reaction mixture was filtrated, stripped of the solvent and subjected to distillation under reduced pressure to give 196 g of cis-9-tetradecene-1-chloride in a yield of about 87% of the theoretical value.

A reaction mixture composed of 115 g of the above obtained cis-9-tetradecene-1-chloride, 120 g of glacial acetic acid and 100 g of anhydrous sodium acetate was heated in a reaction vessel of 1 liter capacity at 164° C. under reflux for 10 hours. After the end of the above reaction time, the reaction mixture was cooled to 50° C. and 300 ml of water were added thereto. The organic solution taken by phase separation of the reaction mixture was distilled under reduced pressure to give 120 g of cis-9-tetra-decenyl acetate having a purity of 98%. The yield was about 95% of the theoretical value. This compound is a well known sexual pheromone compound of several kinds of noxious insects such as smaller tea tortrix, summer fruit tortrix, almond moth and the like.

What is claimed is:

1. Cis-6-undecene-1-chloride expressed by the structural formula

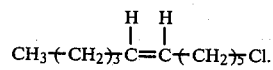

2. A method for the preparation of cis-6-undecene-1-chloride which comprises the steps of
    (a) reacting cis-3-octene-1-chloride with metallic magnesium in tetrahydrofuran to give cis-3-octenylmagnesium chloride, and
    (b) reacting the cis-3-octenylmagnesium chloride with 1-bromo-3-chloropropane in the presence of a lithium copper chloride as a catalyst.

3. The method as claimed in claim 2 wherein the lithium copper chloride is dilithium copper tetrachloride $Li_2CuCl_4$ or lithium copper dichloride $LiCuCl_2$.

4. The method as claimed in claim 2 wherein the amount of the lithium copper chloride is in the range from 0.001 to 0.1 mole per mole of the cis-3-octenylmagnesium chloride.

* * * * *